United States Patent [19]

Shaffer

[11] Patent Number: 5,333,044

[45] Date of Patent: Jul. 26, 1994

[54] FLUORESCENT IMAGE TRACKING VELOCIMETER

[75] Inventor: Franklin D. Shaffer, Library, Pa.

[73] Assignee: The United States of America as represented by the Department of Energy, Washington, D.C.

[21] Appl. No.: 980,894

[22] Filed: Nov. 24, 1992

[51] Int. Cl.$^5$ .......................... G01P 3/36; A61B 5/00; G01F 1/00

[52] U.S. Cl. ..................................... 356/28; 128/633; 128/661.08; 250/356.1

[58] Field of Search .............. 250/356.1; 356/28, 28.5; 128/633, 661.08

[56] References Cited

U.S. PATENT DOCUMENTS

| | | | |
|---|---|---|---|
| 4,919,536 | 4/1990 | Komine | 356/28.5 |
| 5,110,204 | 5/1992 | Miles et al. | 356/28 |
| 5,153,665 | 10/1992 | Weinstein | 356/28 |
| 5,208,651 | 5/1993 | Buican | 356/346 |

OTHER PUBLICATIONS

Shaffer et al., "Flow Visualization of the Novacor Left Ventricular Assist System", Proceedings of the Cardiovascular Science and Technology Conf., Dec. 2–4, 1991.
Woodard et al., "Optimal Management of a Ventricular Assist System: Contribution of Flow Visualization Studies", Proceedings of the American Society of Artificial Internal Organs, May 6–9, 1992.
Shaffer et al., "Fluorescent Image Tracking Velocimetry Applied to the Novacor Left Ventricular Assist Device", Proceedings of the ASME Fluids Engineering Meeting, Jun. 21–23, 1992.

Primary Examiner—Stephen C. Buczinski
Attorney, Agent, or Firm—Hugh W. Glenn; Robert J. Fisher; William R. Moser

[57] ABSTRACT

A multiple-exposure fluorescent image tracking velocimeter (FITV) detects and measures the motion (trajectory, direction and velocity) of small particles close to light scattering surfaces. The small particles may follow the motion of a carrier medium such as a liquid, gas or multi-phase mixture, allowing the motion of the carrier medium to be observed, measured and recorded. The main components of the FITV include: (1) fluorescent particles; (2) a pulsed fluorescent excitation laser source; (3) an imaging camera; and (4) an image analyzer. FITV uses fluorescing particles excited by visible laser light to enhance particle image detectability near light scattering surfaces. The excitation laser light is filtered out before reaching the imaging camera allowing the fluoresced wavelengths emitted by the particles to be detected and recorded by the camera. FITV employs multiple exposures of a single camera image by pulsing the excitation laser light for producing a series of images of each particle along its trajectory. The time-lapsed image may be used to determine trajectory and velocity and the exposures may be coded to derive directional information.

17 Claims, 10 Drawing Sheets 60 b/min, 55 ml SV 80 b/min, 41 ml SV 120 b/min, 28 ml SV 140 b/min, 24 ml SV

FLUORESCENT IMAGE TRACKING VELOCIMETER

The United States Government has rights in this invention pursuant to the employer-employee relationship of the Government to the inventor as a U.S. Department of Energy employee at the Pittsburgh Energy Technology Center.

FIELD OF THE INVENTION

This invention relates generally to the analysis of fluid flow through a fluid carrying body and is particularly directed to observing and measuring flow fields in confined areas and particularly adjacent to surfaces such as the flow of blood or a blood simulation fluid bounded by a wall of biomaterial.

BACKGROUND OF THE INVENTION

The Institute of Medicine recently estimated that between 35,000 and 70,000 Americans annually require either permanent circulatory assist devices or cardiac transplantation. For these patients, the therapy of choice remains cardiac transplantation. However, the donor heart supply is severely limited (1,673 cardiac transplants were performed in the United States in 1989) and is expected to remain so into the foreseeable future. Thus, development of circulatory assist devices is critical to the survival of most of these heart-failure patients.

For the last 25 years, much of the work to develop circulatory assist devices has involved pulsatile pumps that mimic the pumping action of the natural heart. Impressive progress has been made in solving the complex problems associated with the safe delivery of blood to the systemic circulation. In fact, several systems are now successfully being used to support terminal cardiac patients who await transplantation. One such device, the Novacor left ventricular assist system (LVAS), has been used to support more than 100 heart-failure patients awaiting transplantation. FIG. 1 is a simplified diagnostic illustration of a LVAS shown implanted in a patient. LVAS 10, employed as a temporary bridge to cardiac transplantation, is coupled to the left ventricle 12 of a human heart 14 and includes an inflow conduit 16, an outflow conduit 18, and a pump/drive unit 20. Respective inflow and outflow valves are located at the connection of the inflow and outflow conduits 16, 18 to the heart's left ventricle 12, although these valves are not shown in the figure for simplicity. LVAS 10 is disposed below the user's diaphragm 22, with the inflow and outflow conduits 16, 18 passing through the diaphragm. Incorporated in LVAS 10 is a microprocessor-based controller for regulating the pumping of blood within the pump/drive unit 20.

Blood-biomaterial interactions are of critical importance to the operation of the LVAS implant. Undesirable formation of thrombus on biomaterial surfaces can lead to critical, sometimes fatal, results. This activation is likely a strong function of patient-dependent factors and the choice of biomaterials, but fluid-dynamic properties of the device are also of great importance. Although the conditions that cause activation are not completely understood, it is believed that high shear rates, areas of flow stasis, and generation of strong recirculation zones are undesirable within any blood contacting device. Understanding fluid flow within the LVAS implant is essential for improving its performance in increasing survivability and enhancing the health of implant users.

The present invention is a significant advance in the area of artificial organs in that it permits observing and measuring in great detail flow fields within an artificial organ such as a LVAS implant and in particular near the biomaterial surfaces within the artificial organ. The present invention has also been successfully applied to analyze flow within the Nimbus AXIPUMP (another type of LXAS) and a type of artificial lung called an intravenous membrane oxygenator. Although disclosed primarily in terms of the analysis of blood flow within an artificial implant organ, the present invention is not limited to this environment, but is equally applicable for the analysis, measurement and recording of fluid flow fields in virtually any transparent fluid transporting device or system.

OBJECTS AND SUMMARY OF THE INVENTION

Accordingly, it is an object of the present invention to observe, measure and record the flow field in a fluid carrying device.

It is another object of the present invention to visualize, measure and quantify the blood flow field in an artificial implant organ such as a heart pump or a lung to determine blood-biomaterial interaction.

A further object of the present invention is to provide a detailed analysis of the flow field in a confined volume and in particular adjacent to and on the fluid confining surfaces.

Yet another object of the present invention is to monitor the flow field in an artificial heart pump under different operating modes to determine optimum heart pump operation for various patient conditions.

A still further object of the present invention is to observe the flow field in an implantable artificial organ under conditions that closely simulate clinically observed hemodynamic conditions of an implanted patient.

It is another object of the present invention to provide flow visualization information about large areas in a fluid transport device such as an artificial blood pump at one time to permit detailed analysis of complex geometries with moving boundaries and imperfect optical surfaces typical of the blood-pump sac.

It is yet another object of the present invention to provide not only a good qualitative view of flow patterns based on moving images in a fluid carrying device, but also to provide numerical values of velocity, shear rate and residence time with suitable illumination and data acquisition techniques.

These objects of the present invention are achieved and the disadvantages of the prior art are eliminated by apparatus for determining the flow field of a fluid near the fluid confining wall of a transparent body. The apparatus comprises a plurality of neutrally buoyant fluorescent particles suspended in the fluid and a source of pulsed monochromatic light for directing a monochromatic light beam on the fluid and on the confining wall for illuminating the fluorescent particles at predetermined time intervals, wherein the monochromatic light beam has a frequency $\lambda_1$ capable of exciting the particles to a state of fluorescence at a frequency $\lambda_2$. The apparatus further includes an optical filter for receiving light scattered from the confining wall having a frequency $\lambda_1$ and fluorescent light having a frequency $\lambda_2$ and for removing the scattered light and passing the fluorescent light and an optical analyzer cooperating with the filter for receiving pulsed fluorescent light from the particles having a frequency $\lambda_2$ and for tracking displacement of the fluorescent particles in the fluid over time in providing a velocity map of the particles in the fluid adjacent to the confining wall of the body.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DETAILED DESCRIPTION

The present invention employs a technique called fluorescent image tracking velocimetry, or FITV. FITV is a particle image velocimetry technique that enables measurements very close to biomaterial surfaces in accordance with the present invention.

Figure 1:
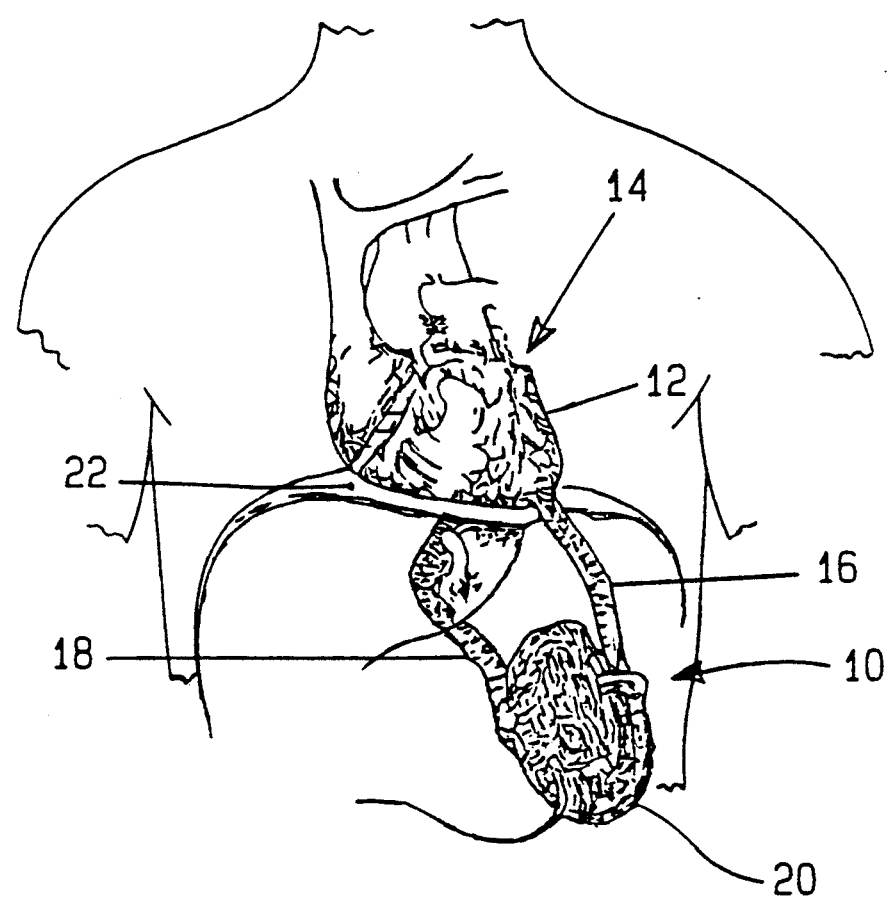
FIG. 1 is a simplified diagrammatic illustration of an artificial blood pump implanted in a human body and attached to that person's heart.

With advances in computer imaging equipment and pulsed lasers, applications of particle image velocimetry are increasing rapidly. Another reason for the popularity of particle imaging velocimetry is its simplicity: a fluid is seeded with particles that follow the fluid flow—that is, neutrally-buoyant particles with low Stokes numbers and sizes much smaller than the length scales of the flow. A simplified schematic diagram of a flow analysis system 30 employing FITV as used in the present invention is shown in FIG. 1. A source of monochromatic light with a frequency $\lambda_1$ such as a pulsed laser 32 illuminates the seeded flow field in a fluid 34 at controlled intervals. The displacement of particles 38 between laser pulses produces a velocity vector map of a flow field. From this, other important parameters, such as shear stress and particle residence time, are attainable.

A wall 36 of the fluid carrying body provides a confining surface 36a for the fluid 34. Light from the pulsed laser 32 at a frequency $\lambda_1$ is scattered by the particles as well as by the confining surface 36a. The fluorescent particles 38, activated by the laser 32, emit light at a frequency $\lambda_2$. An excitation filter 40 removes the $\lambda_1$ light allowing only the $\lambda_2$ light to reach a camera 42.

Although the underlying concept of particle imaging velocimetry appears to be straightforward, considerable problems must be addressed and resolved. The main difficulties are in the acquisition of images with good signal-to-noise (S/N) ratios near flow boundaries and the digital analysis of images.

There are many variations of particle imaging velocimetry. A double-pulse technique is known as particle image velocimetry or PIV. PIV produces a two-dimensional velocity map at an instant. The double-pulse technique has good spatial resolution but derives only the speed and orientation of velocity vectors—direction (sign) is unknown. A coded pulse sequence is one way to eliminate directional ambiguity. However, pulse coding often requires longer exposures and more pulses. This reduces spatial resolution due to the increased number and size of particle images. Yet another particle imaging velocimetry approach uses continuous pulsed illumination to produce Lagrangian trackings of particles through a flow field.

Refractive/reflective light scattering is adequate for most particle imaging applications. With enough illumination power, good signal-to-noise (S/N) ratios between particle images and the background are achievable. Near solid flow boundaries, however, the S/N ratio may diminish to the point that particle images are undetectable. This is because scattering (refractive/reflective scattering will simply be referred to as scattering) from solid flow boundaries is usually much stronger than from small particles. Even if the refractive indices of the fluid and flow boundary are matched, impurities in the solid flow boundary can still generate strong scattering.

Figure 2:
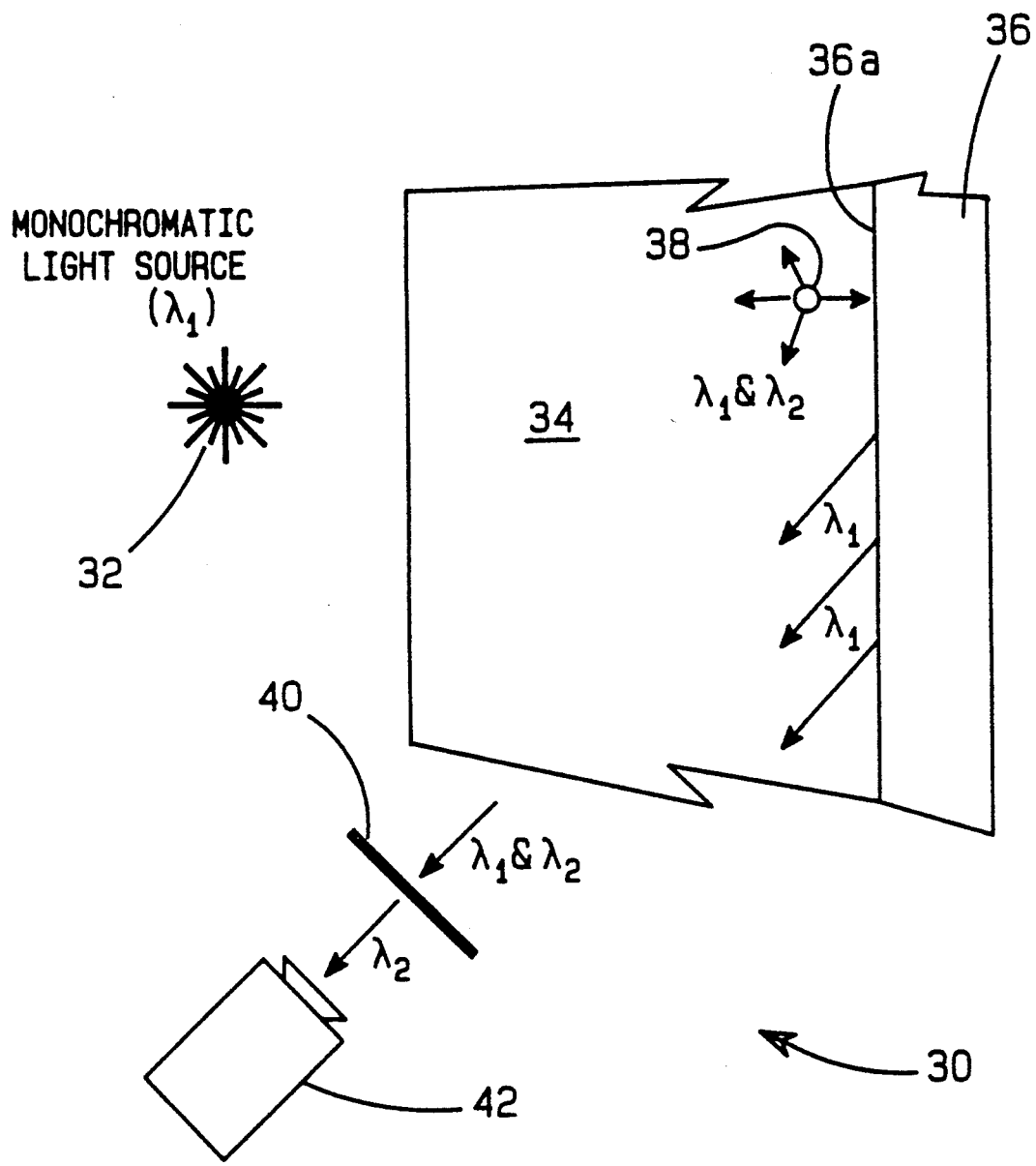
FIG. 2 is a simplified schematic diagram of a flow analysis system illustrating the basic concept of the fluorescent image tracking velocimeter of the present invention.

The use of fluorescent particles and color filtering is one way to enhance S/N ratios near flow boundaries. When excited with light of an appropriate wavelength, the dye fluoresces or emits light. An important property of the fluorescent dye is its Stokes shift—the difference between excitation and emission wavelengths. Thus, the light from the particle shown in FIG. 2 consists of both scattered light at the excitation wavelength ($\lambda_1$) and fluoresced light at a different wavelength (mean fluorescent emission, $\lambda_2$). The light scattered by the flow boundary in FIG. 2 is at the same wavelength as the excitation light.

The S/N ratio is increased dramatically by placing an excitation filter 40 in front of the camera 42. The excitation filter 40 occludes the light scattered by the flow boundary and the particle at $\lambda_1$—the camera sees only the fluorescent light emitted by particles at $\lambda_2$. This has provided excellent S/N ratios of particles close to biomaterial surfaces such as in a LVAS.

Figure 3:
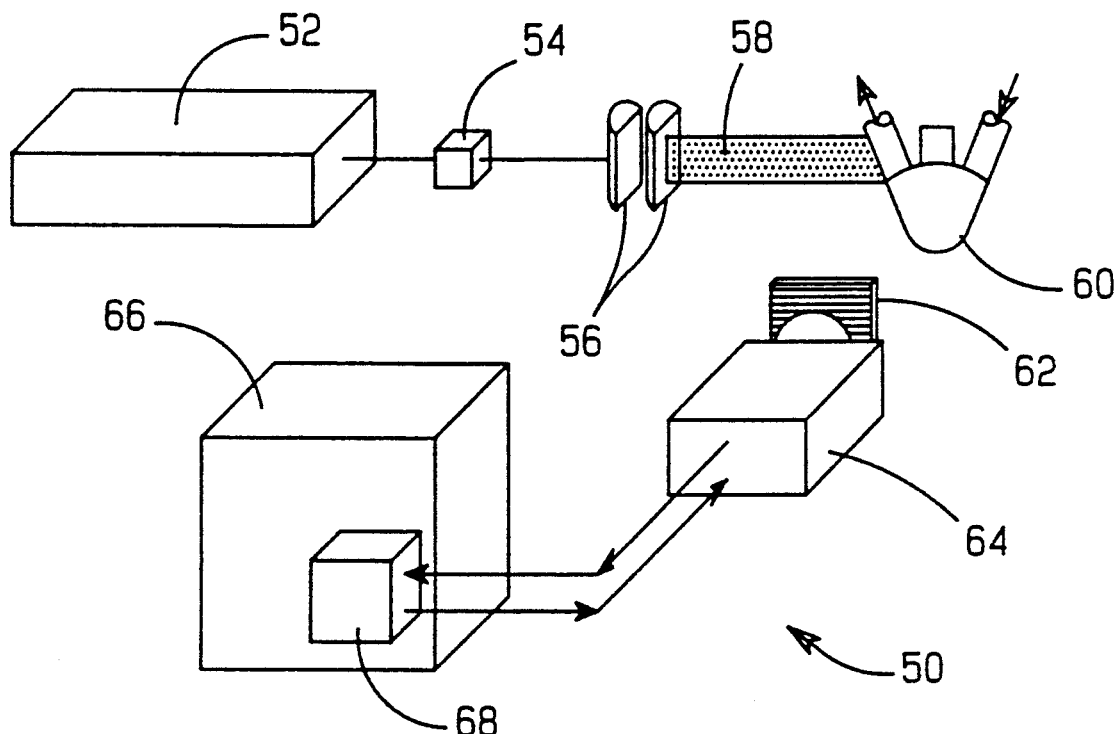
FIG. 3 is a simplified combined block and schematic diagram of a fluorescent image tracking velocimeter in accordance with the principles of the present invention.

Referring to FIG. 3, there is shown a simplified combined schematic and block diagram of a fluorescent image tracking velocimeter (FITV) 50 in accordance with the principles of the present invention. FITV 50 includes a pulsed excitation source such as either a pulsed copper-vapor laser 52 or a copper-vapor continuous argon laser 52 in combination with an acousto-optic modulator 54. The pulsed laser beam is directed through beam shaping optics such as a pair of cylindrical lenses 56 for converting the beam into a rectangular cross section with a large aspect ratio known as a laser sheet 58 and then sent to an artificial heart pump 60 for flow analysis of a fluid therein. An electronic camera 64 with a digital image acquisition system detects and records the particle velocity image within the artificial heart pump 60 through an excitation occlusion filter 62 which screens out the excitation wavelengths and passes only the fluorescent wavelengths. An image processing computer system 66 including a parallel image processing subsystem 68 processes and analyzes the FITV images. Each of these components of FITV 50 is described in greater detail in the following paragraphs.

Excitation Light Sources. The wavelength of the light source should be close to the peak excitation wavelength of the fluorescent dye. The excitation light source must produce pulsed light with accurate and controllable pulse timing. Continuous emission lasers with an acousto-optical modulator are ideal. Experience indicates that at least 1 watt of power is necessary for FITV.

For this application, the excitation source is preferably either an argon or a copper-vapor laser. The argon laser produces up to 5 watts of continuous light with the most powerful wavelengths (nm) at 488 (blue) and 514.5 (green). Other less powerful lines are present at wavelengths from 350 nm to 507.1 nm.

An electronically controlled acousto-optic modulator (AOM) pulses the continuous beam of the argon laser. The AOM transmission rise time limits the AOM pulse capabilities. With a rise time of less than 50 ns, the AOM pulses can range from continuous transmission to repetition rates over 1 MHz and pulse durations less than a microsecond.

The copper-vapor laser is pulsed with pulse durations of 30 ns and repetition rates of up to 20 KHz. Pulse energies range from 0.5 to 2 mJ. The copper-vapor laser produces two primary wavelengths of 510.6 and 578.2 nm with a total average optical power of 10 W. Only the 510.6 nm wavelength is used for this application. The copper-vapor laser is used only if the required pulse durations become short enough that the pulse energies from the argon laser drop well below 0.5 mJ.

Beam shaping optics. The beam shaping optics consist of a series of cylindrical lens 56. They transform the circular cross section of the beam into a rectangular cross section with a large aspect ratio. This is commonly called a laser sheet 58.

Figure 4:
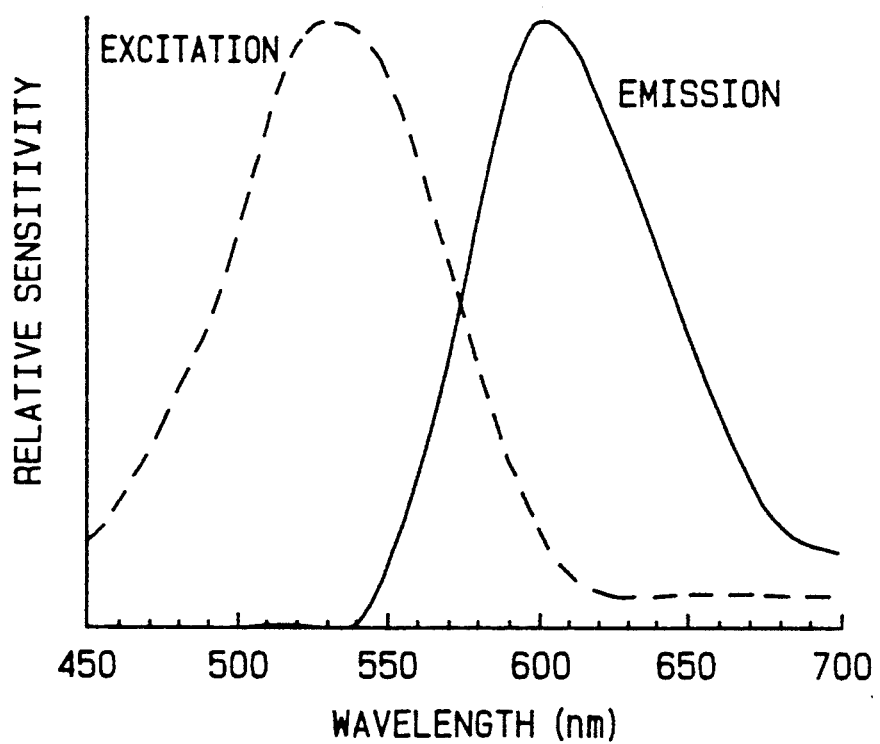
FIG. 4 is a graphic representation of the excitation and emission spectra of a typical commercial fluorescent-dyed particle used in the present invention.

Fluorescent-Dyed Particles Fluorescent particles are available from several commercial manufacturers. Some of the commercial manufacturers are Polyscience, Duke Scientific, and Bangs laboratories. FIG. 4 is a graphic illustration of the excitation and emission characteristics of a commercial fluorescent particle. The dye in this particle is suitable for excitation with the green wavelengths of argon (514.5 nm) and copper-vapor (510.6 nm) lasers. Other fluorescent-dyed particles are available for excitation with lasers of different wavelengths.

Figure 5:
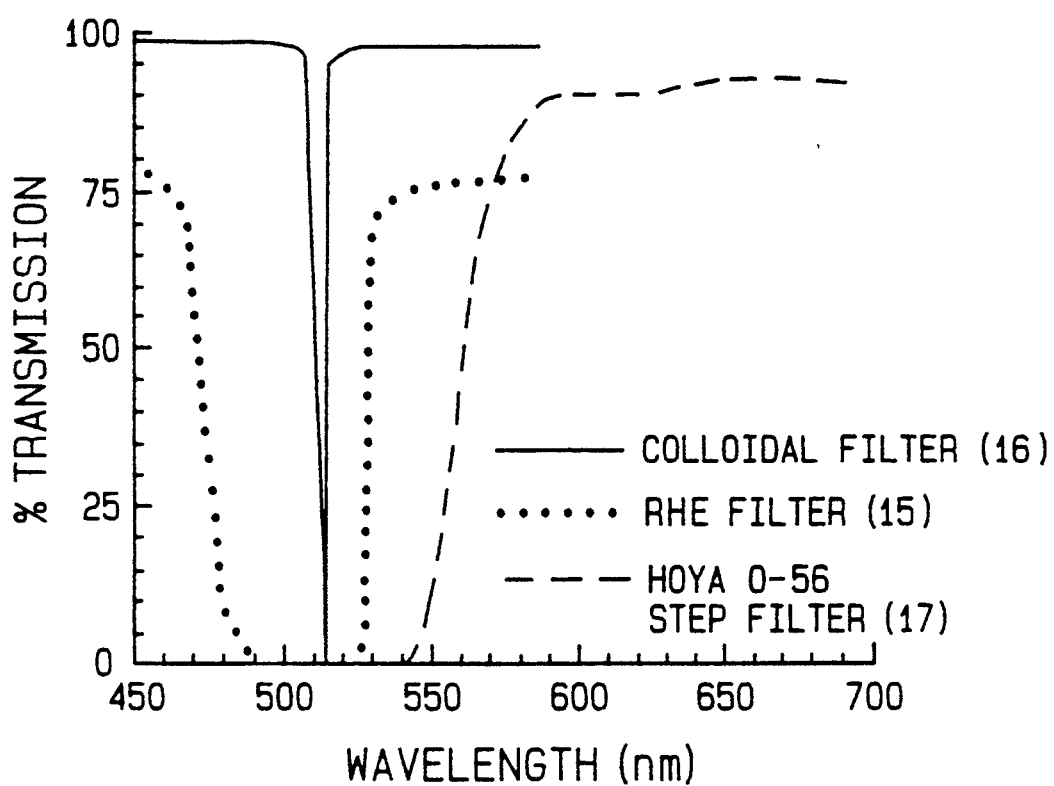
FIG. 5 is a graphic illustration of the transmission characteristics in the form of transmission spectra for notch and step filters employed in the present invention.

Excitation Filters. The purpose of the excitation filter 62 is to occlude the excitation wavelength(s) and pass the fluorescent wavelengths. With monochromatic excitation, the ideal filter will block only a single wavelength. Three types of filters approach monochromatic occlusion: thin-film dielectric interference filters, Raman holographic edge (RHE) filters, and colloidal Bragg diffraction filters. The mean occlusion characteristics of the interference and RHE filters are practically the same. The transmission characteristics of an RHE and a colloidal filter are shown in FIG. 5.

Since the Stokes shift is significant ('20 nm) for many fluorescent dyes, an edge filter can possibly be used. Edge filters are much less expensive than the notch filters. FIG. 5 also shows the transmission curve of an inexpensive edge filter.

Image acquisition system. The camera employed in this embodiment of FITV 50 is a MTI Model 81 tube camera. The camera scanning parameters are externally controlled through an ANDROX programmable video controller 68. An ANDROX analog-to-digital converter (ADC) digitizes the analog output of the MTI 81. With this setup, image resolutions from 512×512 pixels to 2048-1800 pixels are attained. The grey-level resolution of each pixel is 8 bits. The frame rate is variable from 10 frames per second (2048×1800 pixel resolution) to 100 frames per second (512×512 pixel resolution).

Image processing computer system. Processing and analysis of FITV images are done on a SUN 470 workstation equipped with an ANDROX parallel image processing subsystem. The ANDROX system accelerates many image processing functions by a factor of 50 or more over the SUN 470 CPU.

Referring back to FIG. 1, the artificial heart pump 10 is placed extraperitoneally within the abdomen, with the inflow conduit 16 connected to the left ventricular apex. The outflow conduit 18 may be anastomosed to either the abdominal aorta as shown in the figure, or to the thoracic aorta. Because the artificial heart pump 10 receives its inflow from the left ventricle, inflow rates are highly variable depending on the contractile status of the myocardium. In the immediate post-operative period, the contractility of the diseased myocardium is additionally depressed by anaesthetic agents. Under these conditions, the ventricle functions almost as a passive conduit and therefore the LVAS inflow is relatively constant. However, because the LVAS allows the myocardium to deliver flow at a greatly reduced afterload, myocardial contractile function may recover and increase beyond pre-implant values within a few days. The ventricle then acts as a "priming pump" for the LVAS, and the inflow to the LVAS becomes markedly pulsatile with peak flow rates of as much as four to five times greater than the immediate post-operative values.

Figure 6:
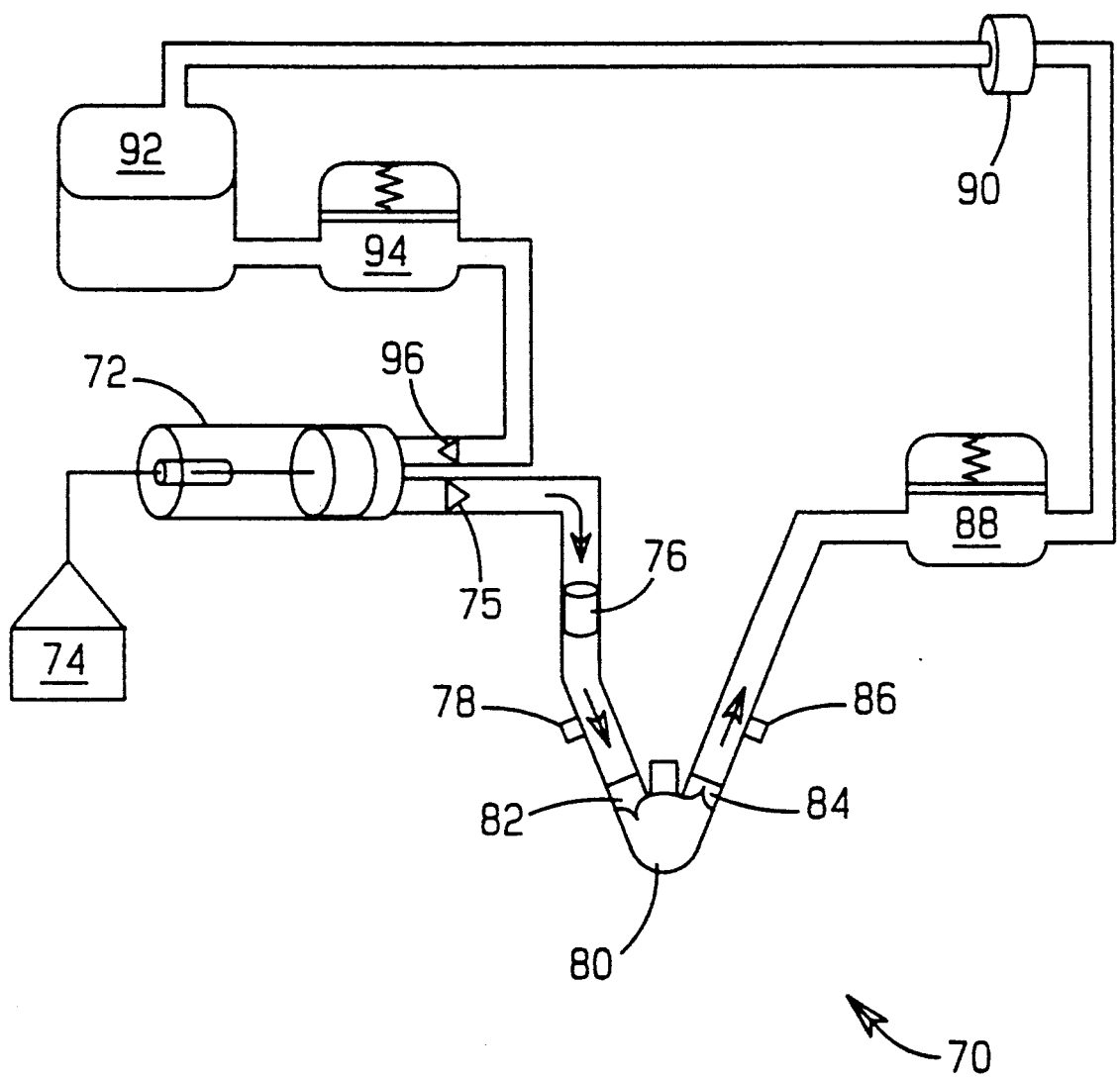
FIG. 6 is a simplified schematic diagram of a cardiac simulation flow loop directing a fluid through an artificial heart pump for analysis by the fluorescent image tracking velocimeter of the present invention.

It is essential to acquire the FITV images under representative patient conditions, including varying degrees of myocardial contractility. For this purpose, an active mock loop 70 shown in simplified schematic diagram form in FIG. 6 has been designed. Inflow to the LVAS 80 is provided by a servo-controlled piston pump 72 coupled to and driven by the combination of a servo-amplifier and computer control 74. This control combination permits the piston pump 72 to produce an arbitrary flow waveform based on a voltage command.

Using a programmable waveform generator, it is possible to generate LVAS inflow waveforms that accurately mimic inflows monitored from patients in an operating room or intensive-care unit.

Flow patterns in the LVAS 80 are also a function of the afterload presented to it. The LVAS afterload in this mock loop uses a calibrated preload compliance 94 coupled to a "venous" reservoir 92 to simulate the systemic vascular compliance and a pneumatic pressure regulator 90 to maintain the mean arterial pressure within physiological values independent of flow, just as occurs in the body via the baroreceptor reflex. The mock loop is instrumented with an ultrasonic transit-time flowmeter 76 and clinical pressure transducers 78 and 86 are coupled to the inflow and outflow valves 82 and 84, respectively, of the LVAS 80. An afterload compliance 88 is coupled between the LVAS output valve 84 and pressure regulator 90, while polyurethane check valves 75 and 96 couple the piston pump 72 respectively to the LVAS 80 and to the preload compliance 94.

The LVAS 80 was manufactured from transparent materials to provide optical access for FITV. A transparent blood analog fluid which has a viscosity close to that of blood (4 cps) was also used. The blood analog fluid consists of a solution of 42% wt. aqueous spectrophotometric-grade glycerin.

The blood analog fluid was seeded with "red" fluorescent particles manufactured by Duke Scientific. The particles consist of polystyrene latex and a proprietary mixture of fluorescent dyes. They are neutrally buoyant and their size is 30±2 microns.

Several filters were tested for the present application. These included an RHE filter and several inexpensive step filters. Rather than attempting an independent measurement of optical density, the performance parameter (S/N ratio) pertinent to this application was measured under typical operating conditions.

The test consisted of measuring the S/N ratios produced with the FITV system for a fixed, representative scene. The scene was a pericardial trileaflet valve in its transparent housing filled with blood analog fluid. The housing, pericardial valve, and blood analog fluid are the same as used in actual flow measurements. The only experimental variable was the type of excitation filter placed in front of the camera lens. The valve is constructed of bovine heart tissue formed into three flexible leaflets that open and close to restrict flow to one direction. The valve leaflet material was found to have mild fluorescent properties. This is undesirable since it increases the background level. Dying the valve with a black clothing dye practically eliminates the valve's fluorescence.

The flow conditions for FITV measurements simulated the full range of clinical conditions typically observed for cardiac transplant patients: pump rates ranged from 60 to 120 beats/minute with fill volumes ranging from 25 to 60 cc.

During a cardiac cycle, the FITV system acquires six images at fixed time separations. For example, if the cardiac cycle duration were 600 ms, six measurements are made at 100 ms separations. After digitizing six images into video RAM, the images are compressed and stored on the SUN 470 hard disk. The acquisition and storage of six FITV images takes about 20 seconds. For a specific experimental condition, data is acquired for at least 100 cardiac cycles.

Figure 7:
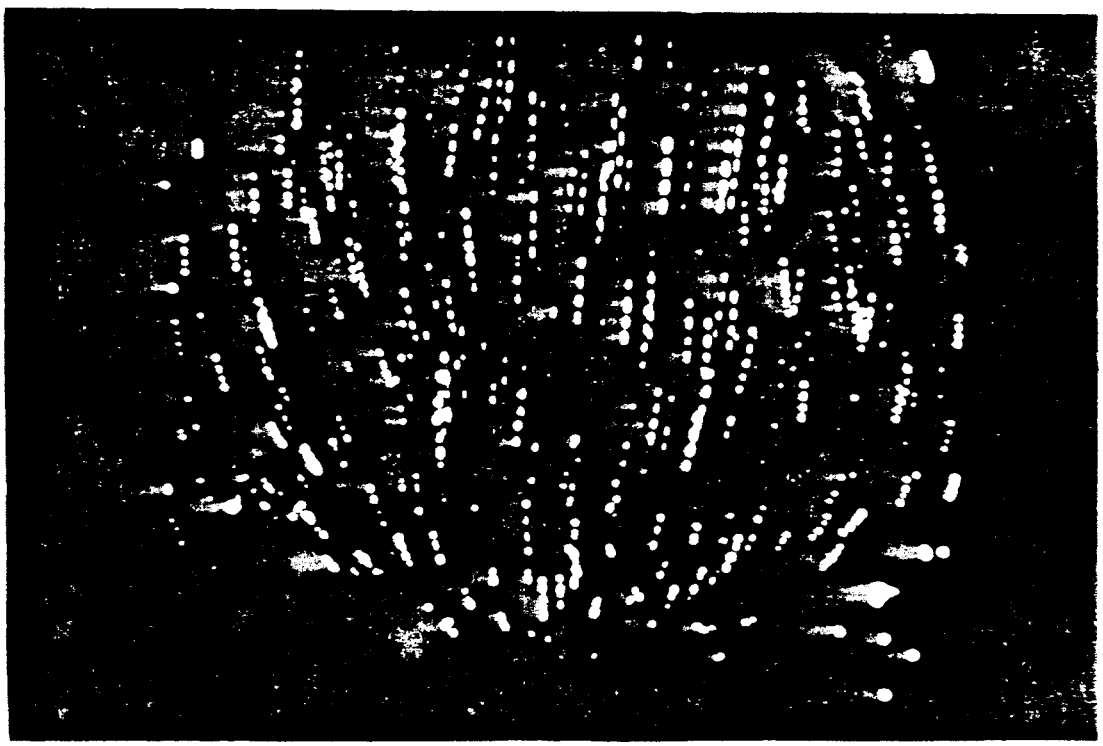
FIG. 7 is an example of a fluorescent image tracking velocimeter image taken 10 milliseconds after the start of systole.
Figure 8:
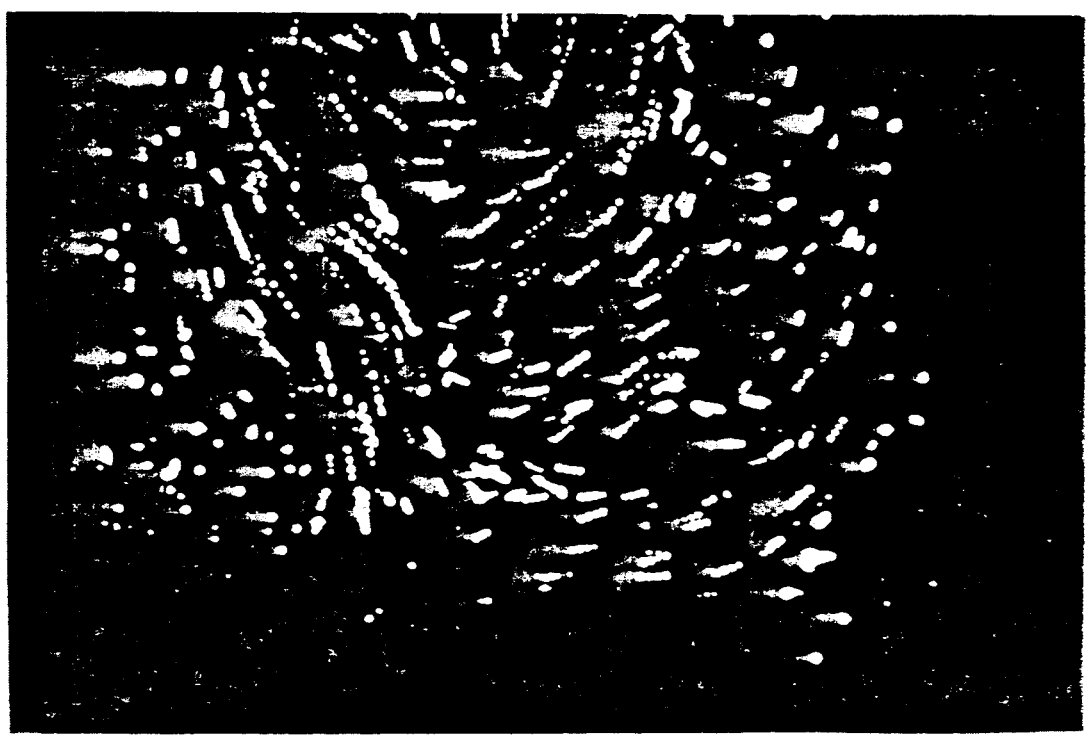
FIG. 8 is an example of a fluorescent image tracking velocimeter image taken by the present invention near the middle of diastole.
Figure 9A:
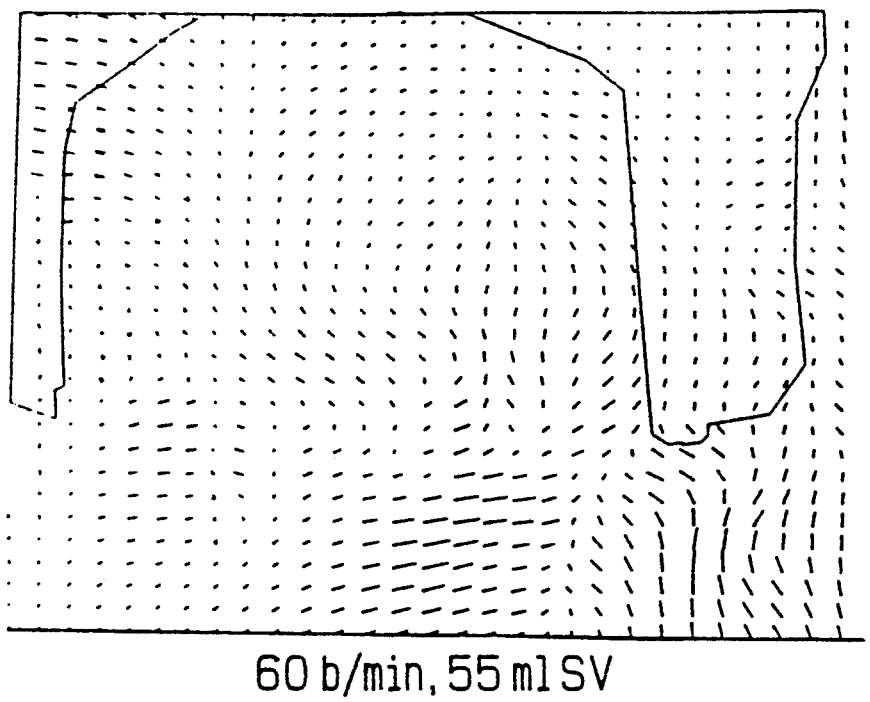
FIGS. 9a-9d illustrate the flow vectors around the inflow valve of an artificial heart pump as measured by the fluorescent image tracking velocimeter of the present invention with identical artificial heart pump output (3.3 l/min), but at different beat rates and stroke volumes.
Figure 9B:
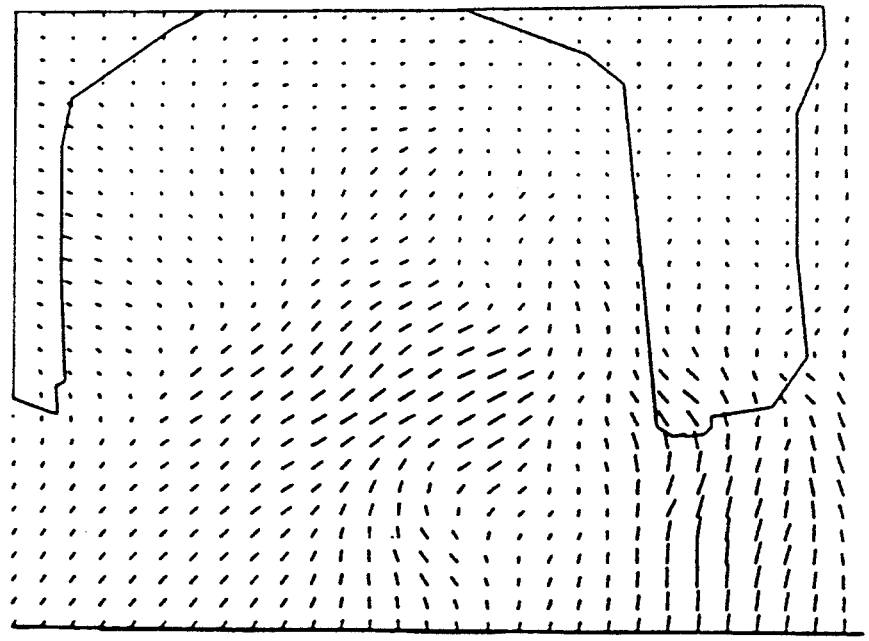
Figure 9C:
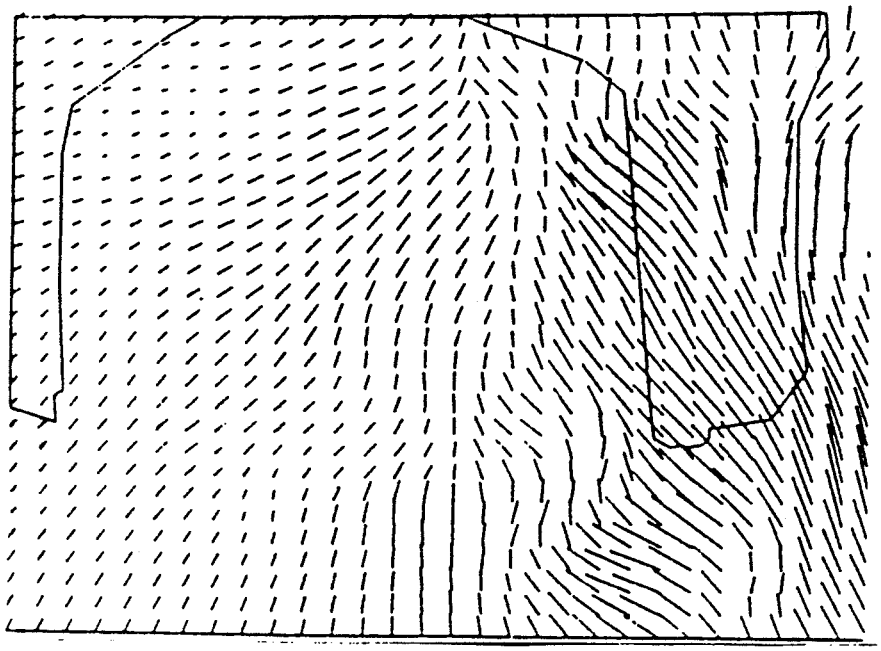
Figure 9D:
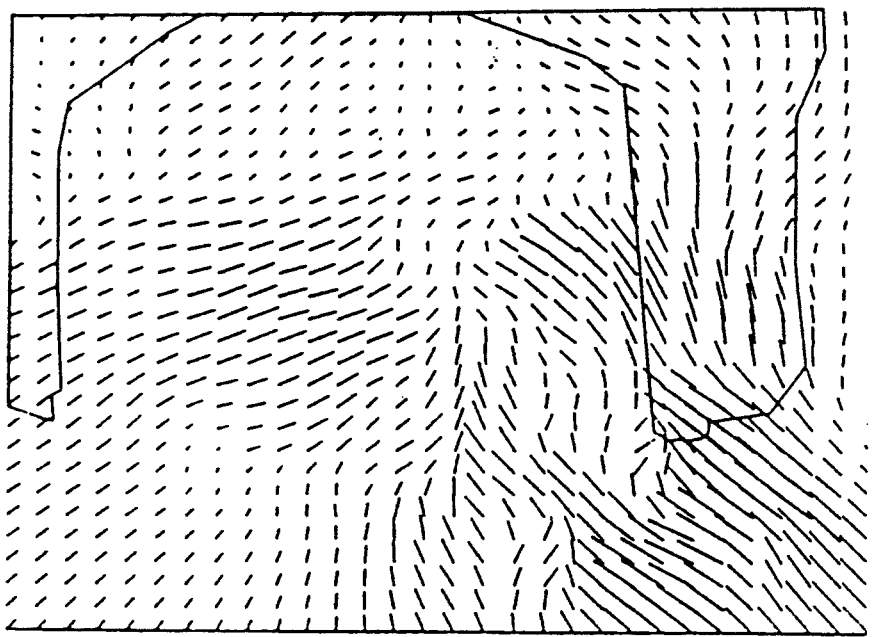
Figure 10:
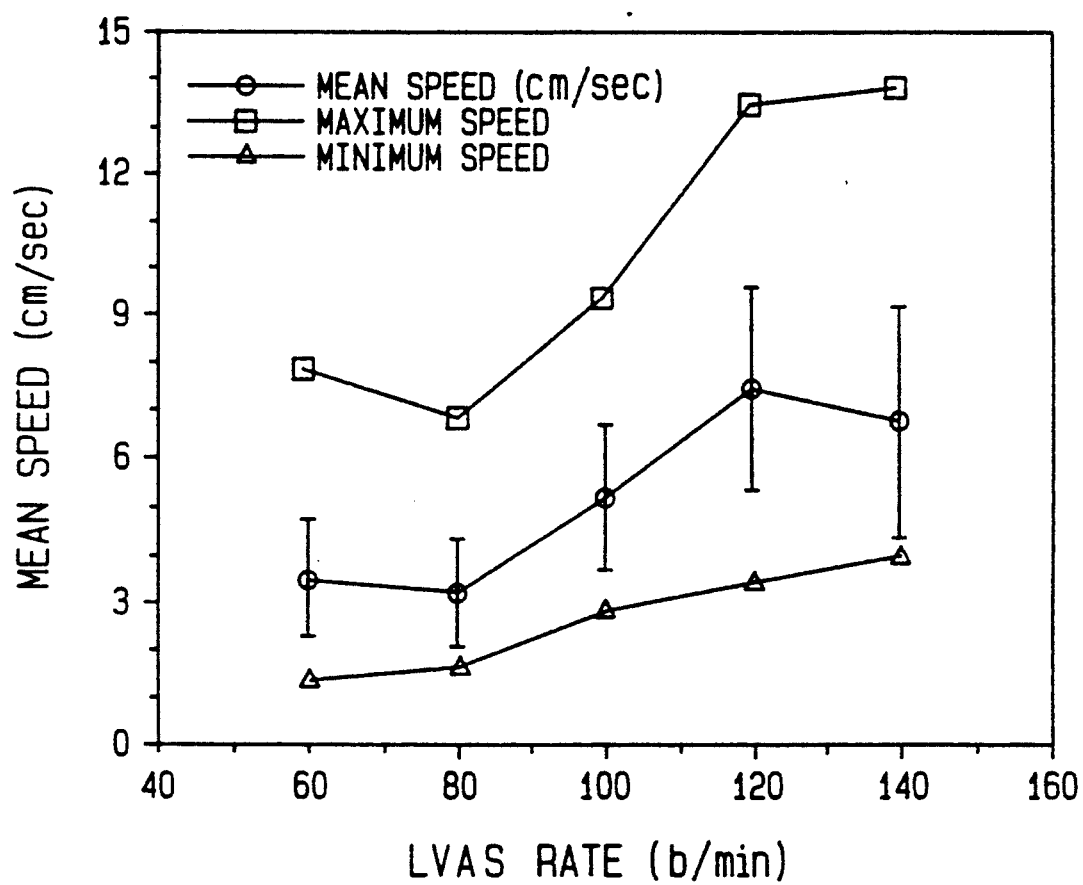
FIG. 10 is a graphic illustration of fluid speed within 1.5 mm of the surface of the inflow valve of an artificial heart pump averaged over three time samples as measured by the fluorescent image tracking velocimeter of the present invention.

FIGS. 7 and 8 show two examples of typical FITV images. FIG. 7 is taken at the beginning of the systole: the flow velocities are high because valve flaps are in motion (closing). FIG. 8 is taken near mid-diastole when the valve flaps are not moving (fully open) and the velocities are much lower. Consequently, to maintain reasonable spacings between consecutive particle images, the laser pulse frequency is varied from frame-to-frame throughout the cardiac cycle. For example, the pulse frequency in FIG. 7 is 1 KHz and in FIG. 8 it is 222 Hz.

Referring to FIGS. 9a-9d, there are shown representations of the flow vectors around the inflow valve of an artificial heart pump for four cases with identical heart pump output (3.3 l/min), but with differing heart rates and stroke volumes. A unit vector of 10 cm/sec is shown in each figure. The valve stents are shown in outline in solid line form in these figures. The lengths of the flow vectors indicate the local speed and the angle of flow is indicated by the vector angle. The flow vectors derived from particle images shown in FIGS. 9a-9d exhibit an ambiguity with respect to the sense of flow direction, i.e., up versus down, left versus right. This ambiguity is due to the symmetric pulse coding of the illumination source. Directional sense can be determined and displayed by a suitable pulse coding technique such as a long pulse of light followed by a series of shorter pulses. Such pulse trains are easily implemented using the electrically-driven acousto-optical modulator described above and a computer-programmed pulse generator. Pulse coding has been successfully implemented for analysis of flow in an artificial lung device.

Effective washing of the prosthetic surfaces within the artificial heart pump is a function of the local shear rates which are, in turn, determined by the fluid velocities. Because the shear rates in this region are much lower than in the valve proper, where the whole stroke volume is forced through a narrow orifice, excessive shear (and consequent application of platelets) is likely less of an issue than the avoidance of stasis. From FIGS. 9a-9d and FIG. 10 which illustrates the variation of fluid speed versus heart pump rate, where fluid speed within 1.5 mm of the surface of the inflow valve has been averaged over the three time instances sampled and where error bars indicate standard deviation, it can be seen that the fluid speed in the vicinity of the inflow valve increases with increasing heart pump beat rate and not with stroke volume under the conditions tested. Maximum speed increases more rapidly than does mean or minimum speed as the beat rate is increased, but the significance of this in terms of stasis is unclear. These data suggest that the flow associated with opening and closing of the inflow valve leaflets is of more importance in the washing of the adjacent areas than is the volume of fluid passing through the valve during each pump cycle. Preliminary studies confirm this finding for the outflow valve area also.

There has thus been shown a fluorescent image tracking velocimeter for visualizing and measuring flow fields adjacent to a fluid confining surface which is particularly adapted for blood flow diagnosis in artificial implantable organs such as a heart pump or lung. Visualization of flow fields adjacent to the biomaterial surfaces in confined areas employs small, neutrally buoyant fluorescent tracer particles for feature extraction. The fluorescent particles are illuminated by a monochromatic laser light source and a filter is used to remove background scattering light before it reaches a scanning camera. Particle motion can then be tracked using parallel image processing software and calculations made of velocities, shear rates and particle residence times in various regions of interest within the artificial implantable organ. Flow measurements can be made under a wide range of conditions simulating the situations observed clinically of both rapid and slow pump filling, including low rates of pump filling typical of the immediate post-operative period which is of critical importance. Other operating modes which can be studied using the fluorescent image tracking velocimeter include (1) internally-triggered automatic synchronous counterpulsation, (2) ECG-triggered synchronous operation, (3) full-to-empty or (4) fixed rate asynchronous operation and an extensive variety of patient hemodynamic conditions.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. Apparatus for determining the flow field of a fluid near a fluid confining wall of a transparent body, said apparatus comprising:
    a plurality of neutrally buoyant fluorescent particles suspended in the fluid;
    a source of pulsed monochromatic light for directing a monochromatic light beam on the fluid and the confining wall for illuminating said fluorescent particles at predetermined time intervals, wherein said monochromatic light beam has a frequency $\lambda_1$ capable of exciting said particles to a pulsed state of fluorescence at a frequency $\lambda_2$;
    filter means for receiving light scattered from said confining wall having said frequency $\lambda_1$ and said fluorescent light having said frequency $\lambda_2$ and for removing said scattered light and passing said fluorescent light; and
    optical means cooperating with said filter means for receiving pulsed fluorescent light from said excited fluorescing particles having a frequency $\lambda_2$ and for tracking displacement of said fluorescent particles in the fluid over time in providing a velocity map of said particles in the fluid adjacent to the confining wall of the body.

2. The apparatus of claim 1 wherein said source of pulsed monochromatic light includes a pulsed copper-vapor laser.

3. The apparatus of claim 1 wherein said source of pulse monochromatic light includes a continuous argon laser in combination with an acousto-optic modulator.

4. The apparatus of claim 1 further comprising beam shaping optics disposed intermediate said source of pulsed monochromatic light and the fluid and the fluid confining wall for converting a circular cross section of said monochromatic light beam to a light beam having a rectangular cross section and a large aspect ratio and for directing said rectangular cross section light beam onto the fluid and fluid confining wall.

5. The apparatus of claim 4 wherein said beam shaping optics includes at least one cylindrical lens.

6. The apparatus of claim 1 wherein said source of pulsed monochromatic light includes an acousto-optic modulator for converting said monochromatic light to a coded light pulse sequence to provide particle displacement direction information in said velocity map.

7. The apparatus of claim 1 wherein said particles include a fluorescent dye.

8. The apparatus of claim 7 wherein said particles are comprised of fluorescent dyed polystyrene latex having a size of 30±2 microns.

9. The apparatus of claim 1 wherein said filter means includes a thin film dielectric interference filter.

10. The apparatus of claim 1 wherein said filter means includes a Raman holographic edge filter.

11. The apparatus of claim 1 wherein said filter means includes a colloidal Bragg diffraction filter.

12. The apparatus of claim 1 wherein said optical means includes a tube camera in combination with an analog-to-digital converter for digitizing an analog output from said tube camera in providing a digital representation of the fluorescent light from the particles.

13. The apparatus of claim 12 wherein said optical means further includes a computer controlled parallel image processor.

14. The apparatus of claim 1 wherein said transparent body is an artificial implantable heart pump.

15. The apparatus of claim 14 further comprising a cardiac flow simulator coupled to said heart pump for providing the fluid thereto over a range of operating conditions corresponding to various patient hemodynamic conditions.

16. The apparatus of claim 1 wherein said transparent body is an artificial lung.

17. Apparatus for viewing and recording a flow field of a fluid in a transparent artificial heart assist pump adjacent a fluid-confining wall in said heart assist pump, said apparatus comprising:
    a plurality of fluorescent particles in the fluid, wherein said particles are neutrally bouyant in the fluid and are approximately the size of human blood cells;
    a source of pulsed monochromatic light for directing a monochromatic light beam having a frequency $\lambda_1$ on the fluid and the fluid-confining wall for exciting said particles whereupon said particles emit fluorescent light having a frequency $\lambda_2$, and wherein said monochromatic light beam is scattered by the fluid-confining wall;
    a cardiac flow simulator coupled to the heart assist pump for providing the fluid thereto under various conditions representing a range of human heart operating circumstances;
    an optical filter for receiving scattered light at a frequency $\lambda_1$ and particle emitted fluorescent light at frequency $\lambda_2$, wherein said optical filter removes the scattered light and transmits the fluorescent light; and
    an optical detector and analyzer combination for receiving the pulsed fluorescent light via said optical filter from said fluorescent particles for providing an image tracking velocity map of the particles adjacent to the fluid-confining wall of the heart assist pump.

* * * * *